US00PP18958P2

(12) United States Plant Patent
Kristensen

(10) Patent No.: US PP18,958 P2
(45) Date of Patent: Jun. 17, 2008

(54) ***OSTEOSPERMUM* PLANT NAMED 'SAKCADNUCOP'**

(50) Latin Name: *Osteospermum hybrida*
Varietal Denomination: Sakcadnucop

(75) Inventor: Niels G. Kristensen, Marslev (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 11/717,339

(22) Filed: Mar. 13, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent Bell
*Assistant Examiner*—S. B. McCormick-Ewoldt
(74) *Attorney, Agent, or Firm*—Jondle & Associates, P.C.

(57) ABSTRACT

An *Osteospermum* cultivar particularly distinguished by its purple-terracotta-copper flower color, large flower size with flowers that remain open under low light conditions and its compact plant growth habit.

1 Drawing Sheet

Genus and species: *Osteospermum hybrida.*
Variety denomination: 'Sakcadnucop'.

BACKGROUND OF THE NEW PLANT

'Sakcadnucop' originated from a hybridization of proprietary hybrid *Osteospermum* breeding line '203005' (unpatented) and commercial hybrid *Osteospermum* line 'Sunny Amanda' (U.S. Plant Pat. No. 16,522) in Aabyhoej, Denmark. The male parent, 'Sunny Amanda', has a pale yellow flower color with terracotta-brown at the flower petal apices, medium flower size and brown disc florets. The female parent, '203005' has a bright yellow flower color, medium flower size and a compact and less branching plant growth habit.

In spring 2003, the two *Osteospermum* lines were crossed and 552 seeds were obtained. The seeds were sown and 442 plants were grown in pots for evaluation. Out of 42 $F_1$ lines, plant number 196 was selected for its unique copper-purple flower color, large flowers which remain open even under low light conditions and dark green plant foliage.

In February 2004, plant number 196 was vegetatively propagated with cuttings and re-evaluated in an open field and a greenhouse. Plant number 196 was given the code number '204056'.

In spring 2004, plants were evaluated again in pots and in an open field. The selection was named 'Sakcadnucop' and found to retain its distinctive characteristics through successive asexual propagations.

SUMMARY OF THE INVENTION

The following are the most outstanding and distinguishing characteristics of this new cultivar when grown under normal horticultural practices in Kakagawa, Japan.

1. Purple-terracotta-copper flower color
2. Large flower size;
3. Flowers that remain open under low light conditions; and
4. Compact plant growth habit.

DESCRIPTION OF PHOTOGRAPHS

This new *Osteospermum* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
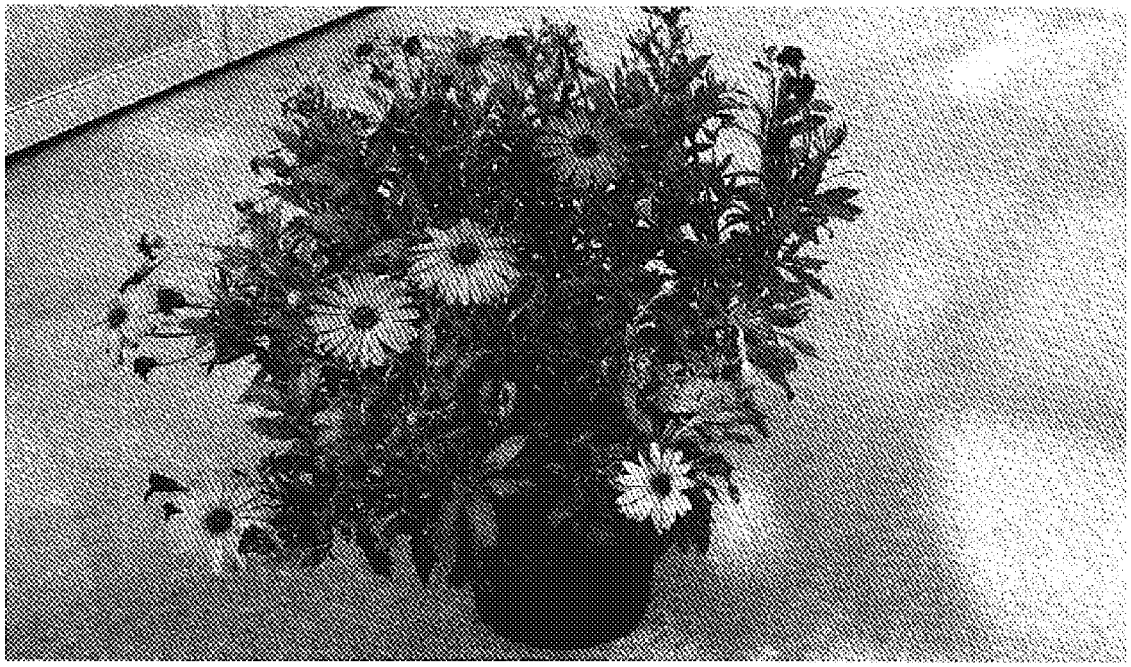
FIG. 1 shows overall plant habit.
Figure 2:
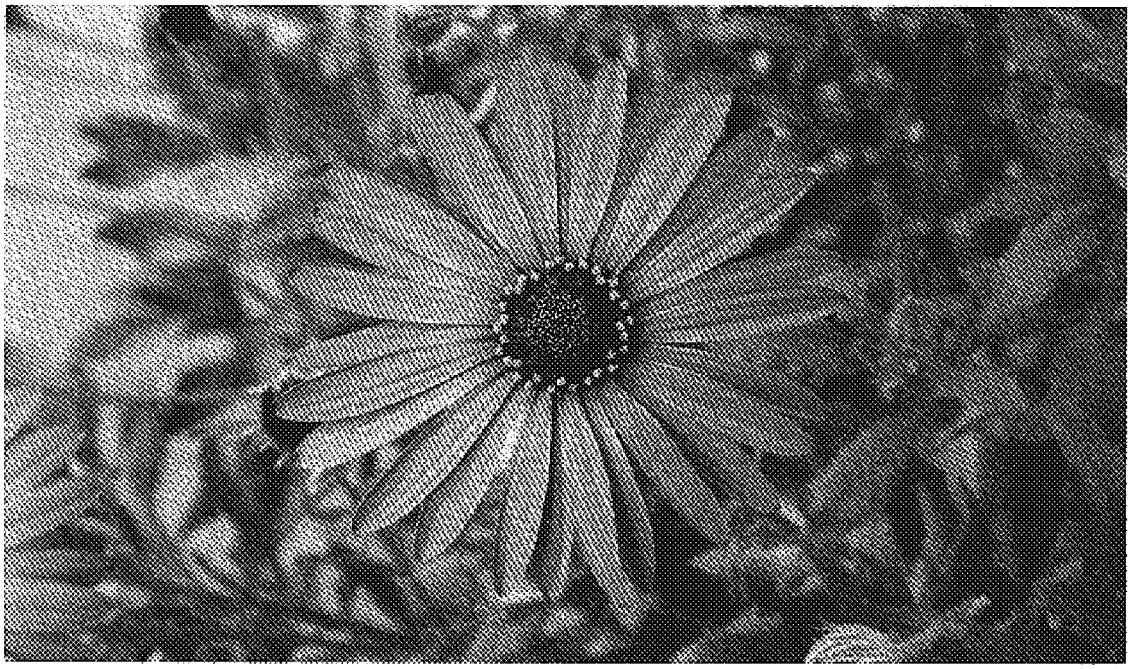
FIG. 2 shows the mature inflorescence.

The following detailed descriptions set forth the distinctive characteristics of 'Sakcadnucop'. The data which define these characteristics were collected from asexual reproductions carried out in Salinas, Calif. Data was collected on plants grown approximately five months from transplanting rooted cuttings into 6-inch pots under greenhouse conditions in Salinas, Calif. Color references are to the R.H.S. Colour Chart of The Royal Horticultural Society of London (R.H.S.).

DESCRIPTION OF THE NEW PLANT

Classification:
*Family.*—Compositae.
*Botanical.*—*Osteospermum hybrida.*

Parentage:
*Female parent.*—Hybrid proprietary *Osteospermum* line '203005' (unpatented).
*Male parent.*—*Osteospermum* line 'Sunny Amanda' (U.S. Plant Pat. No. 16,522).

Growth:
*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root-inducing solution in water. The trays are misted hourly during rooting.
*Environmental conditions for plant growth.*—Rooted cuttings are transplanted to pots with a 16 cm diameter, one plant per pot. Peat-based growing media is used. The pots are watered using a 150-200 ppm fertilizer solution containing 18% nitrogen, 8% phosphorus and 18% potassium. The soil is allowed to dry between waterings. During the first few weeks after transplanting, the plants should have evening temperatures around 15-18° C. for good root growth.

When plants reach 7.5-10 cm in height they are pinched back to 5-6 leaves to promote branching. Spring and summer daytime high temperatures in Salinas, Calif., where the data was collected, range from 16-25° C.

*Time to bloom from propagation.*—Approximately four weeks when rooted vegetative cuttings are transferred to a 16 cm. diameter pot. Flowering season is all year in the United States. Vernalization is not required to induce flowering.

Plant description:

*Habit.*—Compact, mounded and branching.
*Life cycle.*—Perennial.
*Form.*—Branching, dense.
*Height.*—43 cm to 48 cm.
*Width.*—40 cm to 50 cm.

Stems:

*Internode length.*—1.5 cm to 3.0 cm.
*Stem description.*—Strong, erect.
*Stem diameter.*—0.4 cm to 0.5 cm.
*Stem color.*—RHS 145A (Yellow-green).
*Pubescence.*—Sparse.
*Pubescence shape.*—Linear.
*Pubescence color.*—RHS N155A (White).
*Anthocyanin color.*—RHS 64A (Red-purple).

Leaves:

*Arrangement.*—Alternate.
*Shape.*—Oblanceolate.
*Apex.*—Acute.
*Base.*—Decurrent.
*Margin.*—Serrate.
*Venation.*—Pinnate.
*Surface.*—Dull, smooth.
*Surface pubescence.*—Present.
*Length.*—7.5 cm to 8.5 cm.
*Width.*—2.5 cm to 3.0 cm.
*Thickness.*—0.1 cm.
*Color.*—Upper surface: RHS 137B (Green). Lower surface: RHS 138B (Green).
*Venation color.*—Upper surface: RHS 144B (Yellow-green). Lower surface: RHS 139C (Green).

Inflorescence:

*Type.*—Capitulum (head); Disc florets are perfect and ray florets are carpellate.
*Flowering habit.*—Determinate.
*Lastingness of flowers.*—3 to 4 days.
*Fragrance.*—None.
*Seed production.*—None observed.
*Diameter.*—7.0 cm to 8.0 cm.
*Depth.*—1.2 cm to 1.5 cm.
*Disc diameter.*—1.5 cm.
*Disc floret number.*—80 to 100 per inflorescence.
*Peduncle length.*—7.5 cm to 11 cm.
*Peduncle diameter.*—0.2 cm to 0.25 cm.
*Peduncle color.*—RHS 144A (Yellow-green).
*Peduncle texture.*—Dull, pubescent.
*Phyllaries.*—Arrangement: 20 to 24 per inflorescence, free, arranged symmetrically. Length: 1.0 cm to 1.2 cm. Width: 0.15 cm to 0.20 cm. Apex: Acute. Margin: Entire. Shape: Linear, acute. Color: Upper surface: RHS 144A (Yellow-green). Lower surface: RHS 145A (Yellow-green).

Ray florets (ligules):

*Corolla.*—One petal per ray floret; only the outer row of florets are the ray florets.
*Number of ray florets per inflorescence.*—21 to 30.
*Petal length.*—3.4 cm to 3.8 cm.
*Petal width.*—0.7 cm to 0.8 cm.
*Petal shape.*—Spatulate.
*Petal apex.*—Obtuse.
*Petal margin.*—Entire.
*Petal color.*—Upper surface: RHS N77B (Purple). Lower surface: RHS 167C (Gray-orange) with streaks of RHS 183A (Gray-purple).
*Petal pubescence.*—Glabrous.
*Ovary.*—Superior.
*Pistil form.*—One style with two stigma branches.
*Pistil length.*—0.3 cm.
*Stigma color.*—RHS 83A (Purple).
*Style color.*—RHS 83A (Purple).

Disc florets:

*Color.*—RHS N89A (Violet-blue).
*Shape.*—Tubular.
*Apex.*—Rounded.
*Surface.*—Smooth, shiny.
*Size.*—Length: 0.5 cm. Width: 0.1 cm.
*Pistil form.*—One style with two stigma branches.
*Ovary.*—Superior.
*Style color.*—RHS 83A (Purple).
*Stigma color.*—RHS 83A (Purple).
*Stamens.*—5, fused into a single tube.
*Anther color.*—RHS 83A (Purple).
*Pollen color.*—RHS 23A (Yellow-orange).

Disease and insect resistance: Very disease resistant, however, plants are susceptible to aphids, thrips, whiteflies and worms.

COMPARISON WITH PARENTAL LINES AND KNOWN CULTIVARS

'Sakcadnucop' is a distinct variety of *Osteospermum* owing to its purple-terracotta-copper flower color, large flower size with flowers that remain open under low light conditions and its compact plant growth habit. 'Sakcadnucop' is distinguished from its parents primarily by ray floret color, flower size and plant growth habit as described in Table 1 below (color references are to The Royal Horticultural Society Colour Chart, 4$^{th}$ edition):

TABLE 1

| Characteristic | 'Sakcadnucop' | Male Parent 'Sunny Amanda' | Female Parent '203005' |
|---|---|---|---|
| Ray floret (ligule) color, upper surface: | RHS N77B (Purple) | Pale yellow terracotta-brown tips | Bright yellow |
| Flower size | Large | Medium | Medium |
| Disc florets color | Brown | Blue | |

'Sakcadnucop' is most similar to the *Osteospermum* plants named 'Iringa' (U.S. Plant Pat. No. 15,632) and 'Wildside' (U.S. Plant Pat. No. 10,603); however, there are differences as described in Table 2 below (color references are to The Royal Horticultural Society Colour Chart, 4$^{th}$ edition):

TABLE 2

| Characteristic | 'Sakcadnucop' | 'Iringa' | 'Wildside' |
|---|---|---|---|
| Petal color: | RHS N77B (Purple) | RHS 71A (Red-purple) | RHS 71A (Red Purple) |
| Inflorescence diameter | 7.0 cm to 8.0 cm | 6.5 cm to 7.0 cm | 5.0 cm to 5.5 cm |
| Habit | Mounded and compact | Mounded, upright and branching | Erect and less compact |

I claim:

1. A new and distinct cultivar of *Osteospermum* plant as shown and described herein.

* * * * *